(12) United States Patent
Berry et al.

(10) Patent No.: US 10,874,900 B2
(45) Date of Patent: Dec. 29, 2020

(54) THRESHOLD-LOAD TRAINER APPARATUS FOR MUSCLES OF THE TONGUE, THROAT AND UPPER RESPIRATORY PATHWAY AND METHODS FOR TREATMENT OF OBSTRUCTIVE SLEEP APNEA AND OTHER DISORDERS

(71) Applicant: UNIVERSITY OF FLORIDA RESEARCH FOUNDATION, INCORPORATED, Gainesville, FL (US)

(72) Inventors: Richard Barnett Berry, Gainesville, FL (US); Paul Wesley Davenport, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 48 days.

(21) Appl. No.: 16/315,469

(22) PCT Filed: Jun. 30, 2017

(86) PCT No.: PCT/US2017/040158
§ 371 (c)(1),
(2) Date: Jan. 4, 2019

(87) PCT Pub. No.: WO2018/009422
PCT Pub. Date: Jan. 11, 2018

(65) Prior Publication Data
US 2019/0308068 A1    Oct. 10, 2019

(51) Int. Cl.
*A63B 23/03*    (2006.01)
*A61F 5/58*     (2006.01)
(Continued)

(52) U.S. Cl.
CPC ............ *A63B 23/032* (2013.01); *A61B 5/224* (2013.01); *A61B 5/4552* (2013.01); *A61F 5/58* (2013.01);
(Continued)

(58) Field of Classification Search
CPC ......... A61B 5/224; A61B 5/4552; A61B 5/58; A61B 23/032
See application file for complete search history.

(56) References Cited

U.S. PATENT DOCUMENTS

| | | |
|---|---|---|
| 2012/0143091 A1 | 6/2012 | Annett et al. |
| 2014/0066258 A1 | 3/2014 | Smead |
| 2016/0144227 A1 | 5/2016 | Bell |

OTHER PUBLICATIONS

International Search Report and Written Opinion in PCT/US2017/040158 dated Sep. 6, 2017.

*Primary Examiner* — Christine H Matthews
(74) *Attorney, Agent, or Firm* — Timothy H. Van Dyke; Wolter, Van Dyke, Davis, PLLC

(57) ABSTRACT

Devices and methods for training the tongue and other muscles of the throat and upper respiratory airway to alleviate symptoms of snoring and the Obstructive Sleep Apnea Syndrome (OSAS) are provided. A threshold-load trainer, or similar device, having a biased tongue resistance pad is used for strengthening the muscles of the tongue to inhibit narrowing or obstruction of the upper respiratory airway, particularly during a state of relaxation or sleep. The threshold-load trainer embodiments of the subject invention can specifically target the genioglossus muscle under the tongue (the major tongue protruder) and other muscles of the throat and upper respiratory pathway, so as to improve muscle tonus.

14 Claims, 12 Drawing Sheets

(51) Int. Cl.
*A63B 21/02* (2006.01)
*A63B 21/065* (2006.01)
*A61B 5/22* (2006.01)
*A61B 5/00* (2006.01)

(52) U.S. Cl.
CPC .......... *A63B 21/023* (2013.01); *A63B 21/065* (2013.01); *A63B 23/03* (2013.01); *A61B 5/4848* (2013.01); *A61B 2562/0247* (2013.01); *A63B 2220/51* (2013.01); *A63B 2220/56* (2013.01); *A63B 2225/52* (2013.01)

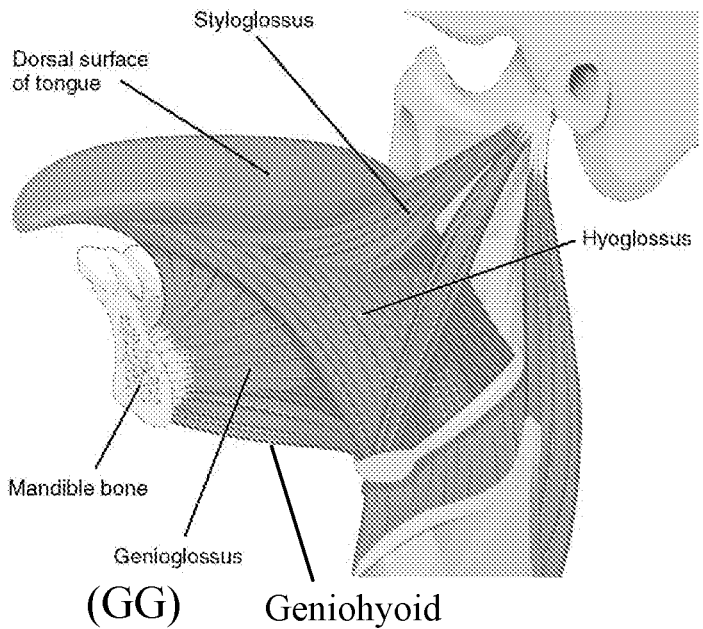
FIG. 3
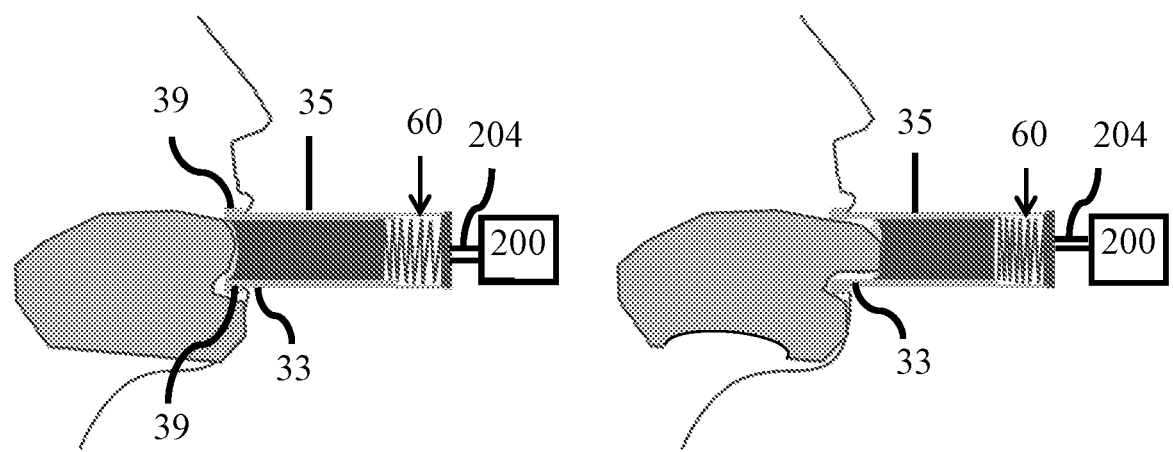
Resting
FIG. 4A
Tongue protrusion
FIG. 4B

FIG. 11A
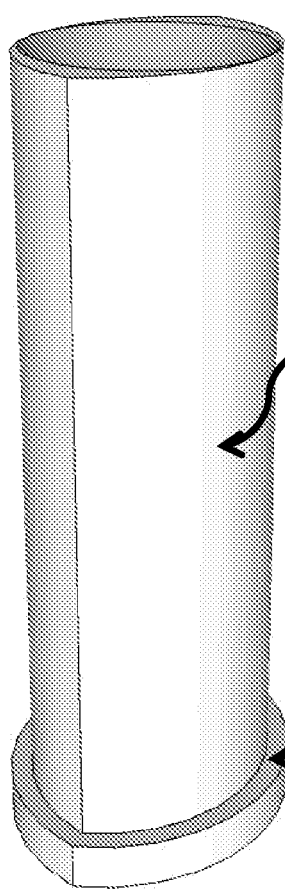
FIG. 11B
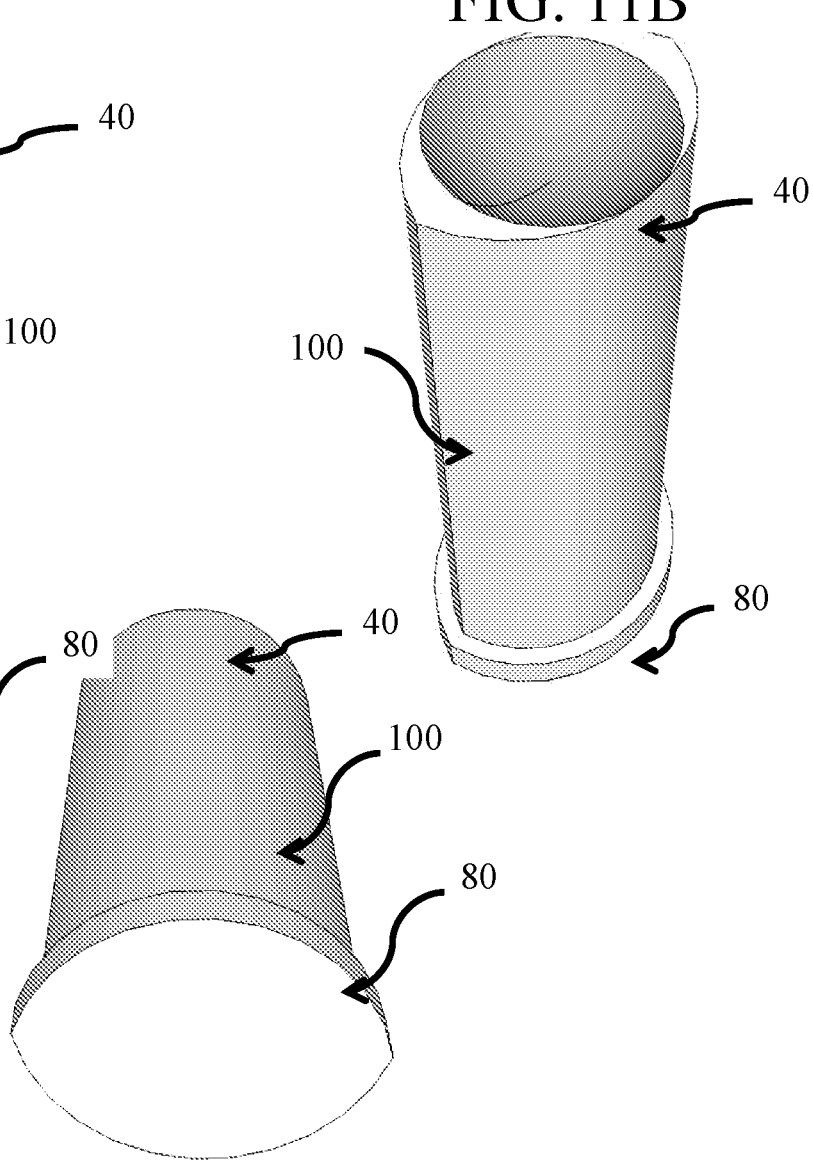
FIG. 11C
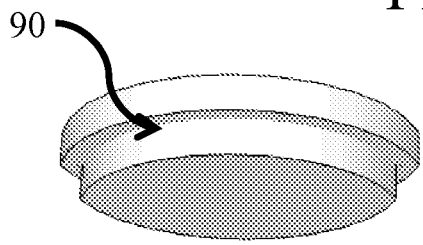
FIG. 12A
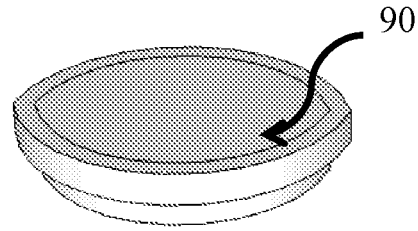
FIG. 12B

THRESHOLD-LOAD TRAINER APPARATUS FOR MUSCLES OF THE TONGUE, THROAT AND UPPER RESPIRATORY PATHWAY AND METHODS FOR TREATMENT OF OBSTRUCTIVE SLEEP APNEA AND OTHER DISORDERS

BACKGROUND OF INVENTION

Obstructive Sleep Apnea Syndrome (OSAS) is characterized by a narrowing or collapse of the upper airway during sleep. This obstruction can be caused by the muscles of the tongue and throat area relaxing and the tongue falling back to block the upper airway. There are a number of treatment devices that can be used for OSAS, including Continuous Positive Airway Pressure (CPAP) machines and various oral appliances, to try to prevent or control OSAS. These devices usually operate by preventing the muscles and tissues of the mouth and throat from falling back into the upper airway.

It has been suggested that strength training of the upper airway muscles such as the palate muscles or tongue can reduce or prevent upper airway obstruction, thereby reducing snoring and the incidence of OSAS. Strengthening these muscles can increase the physiological condition called "tonus," which is the continuous and passive partial contraction of a muscle during resting state. Increasing muscle strength will increase the tonus or the resistance of the muscle to stretching during rest. Increasing tonus in the upper respiratory airway muscles and especially the tongue can prevent them from obstructing the airway when relaxed during sleep.

Previous upper respiratory airway muscle and tongue training devices have been developed, but often do not target the appropriate function of upper airway and tongue muscles. Current upper airway muscle training devices have primarily focused on improving vertical pressure strength by causing the tongue to push upward against the upper palate or forward and upward against the back of the front teeth. However, these exercises do not sufficiently target the protrusive function of genioglossus muscle. The genioglossus muscle is an extrinsic tongue muscle with a flat, fan-shape that runs from the front of the lower jaw into the tongue from tip to base. The genioglossus forms the bulk of the tongue muscles. Contraction of this tongue muscle makes the tongue stick out as its whole foundation is pulled forward (tongue protrusion). By increasing the strength of the genioglossus muscle for protruding the tongue, the natural increase in tonus can decrease the posterior movement of the tongue and the narrowing of the upper airway when this muscle relaxes.

While improved strength of the genioglossus muscle of the tongue can help reduce OSAS, it can also benefit patients who have undergone head or neck surgeries that affect the muscles of the upper respiratory airway (including the tongue). Patients with neuromuscular disorders that affect swallowing and speech therapy patients may also benefit from a device that targets and strengthens the genioglossus muscle of the tongue and other muscles of the throat and upper respiratory pathway. During tongue protrusion training, other muscles such as the geniohyoid increase in strength and tone. Increased tonus also causes a natural shortening of the geniohyoid and other neck muscles, which can reduce the appearance of a double-chin and improve the shape of the jaw line.

BRIEF SUMMARY

In accordance with embodiments described herein, the subject invention pertains generally to a training device for improving the strength of the respiratory muscles, particularly the muscles of the tongue. The embodiments of the subject invention successfully address the disadvantages associated with the previously known tongue strengthening devices and their methods of use and provide certain attributes and advantages that have not been realized by other known devices. In particular, there is provided a novel and highly effective tongue training device and methods of use that can target the genioglossus, a major tongue muscle forming the bulk of the underside of the tongue, to improve the horizontal or protrusive strength and increase the tonus of that muscle and other muscles of the throat and upper respiratory pathway. Advantageously, such improvement to the strength and tonus of the genioglossus tongue muscle (and other muscles of the throat and upper respiratory pathway) can reduce or correct, among other medical issues, snoring and the incidence or severity of the Obstructive Sleep Apnea Syndrome (OSAS) in patients. Strengthening the genioglossus/geniohyoid muscle and other muscles of the throat and upper respiratory pathway can also tighten the chin floor and reduce the appearance of a sagging chin or a double-chin. Additionally, the device can also be used with patients having neuromuscular disorders that affect swallowing or patient undergoing speech therapy to strengthen the muscles of the tongue.

In general, the device can be configured as a threshold-load trainer for the tongue that can specifically target the genioglossus muscle, but can also affect other mouth, jaw, and respiratory muscles. One embodiment includes a mouthpiece for insertion into the mouth and a biasing element operably engaged with a tongue resistance pad against which the tongue can be exerted to apply pressure to the biasing element. The motion of extending the tongue and the resistance of the biasing element can strengthen the genioglossus muscle. It is typically not necessary for the tongue to be fully extended from the mouth and results can be achieved by extending the tongue only a few centimeters past the teeth. A force measuring device can be used to determine the amount of compression force applied to the tongue resistance pad. Pressure sensors can also be used to receive and transmit information about the amount of pressure applied to the biasing element by the tongue resistance pad. Pressure sensors can operate with a pressure transducer that can translate the information from the sensors into a discernable measurement. This can be an indication of how strong the tongue muscles are, particularly the genioglossus muscle.

The methods of the subject invention, in general, pertain to using the threshold-load trainer device by inserting one end of the mouthpiece into the mouth so that the tongue can contact the tongue resistance pad. The tongue tip can push against the tongue resistance pad, thereby depressing it into the mouthpiece to compress the biasing element. By repeatedly depressing the tongue resistance pad, the genioglossus muscle can become stronger and develop desirable tonus. Various isotonic and isometric exercises can be employed to strengthen the genioglossus muscle, as well as other muscles of the upper respiratory airway, mouth, and throat. Over time, the tonus in the genioglossus muscle can increase causing it to shorten and hold the tongue away from the back of the throat (opening the upper airway), even in a relaxed or resting state. This can improve or correct OSAS and other medical conditions caused by a weak genioglossus muscle that can allow the tongue to fall back into or otherwise obstruct the upper airway.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to or implication of dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIG. 1A shows the threshold-load trainer with a tongue resistance pad biased towards the proximal end of the bore. FIG. 1B shows the threshold-load trainer with the tongue resistance pad pushed into the bore.

FIG. 3 illustrates the location of the genioglossus muscle (GG) and how it can be used to extend the tongue.

FIGS. 4A and 4B illustrate an embodiment of the threshold-load trainer of the subject invention in use in the mouth of a patient. In FIG. 4A, the proximal end of the threshold-load trainer is positioned within the mouth so that the tongue can contact the tongue resistance pad, which is biased towards the proximal end. FIG. 4B shows how the tongue can be used to push the tongue resistance pad into the bore of the threshold-load trainer, so as to compress the biasing element. It can be seen that when the tongue protrudes from the mouth, the genioglossus muscle is raised up from the chin area.

FIG. 5B also illustrates an example of sensors within the mouthpiece that can transmit information regarding the biasing element and/or tongue resistance pad to a pressure transducer. FIG. 5D is an elevation view of the proximal end.

FIGS. 11A, 11B, and 11C illustrate a side elevation view, proximal end perspective view, and a distal end perspective view, respectively, of an embodiment of a reciprocating plunger of the subject invention.

FIGS. 12A and 12B illustrate a proximal end perspective view and a distal end perspective view, respectively, of a cap embodiment of the subject invention.

DETAILED DISCLOSURE

Figure 1A:
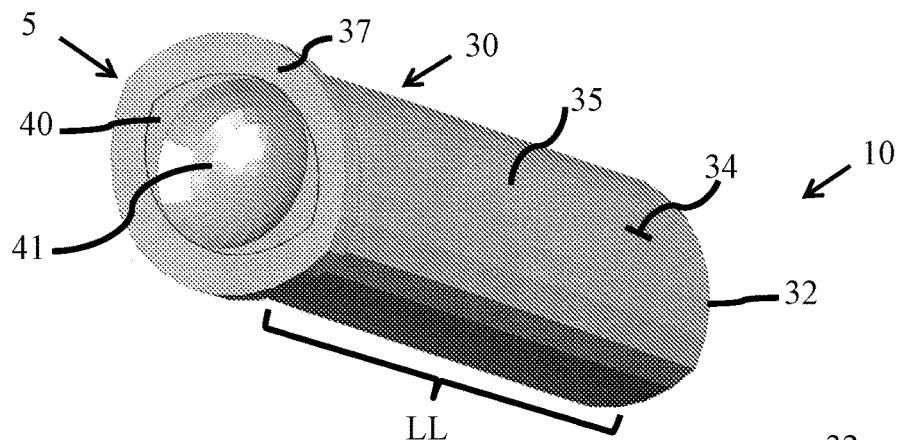
FIGS. 1A and 1B illustrate one embodiment of a threshold-load trainer of the subject invention.

The subject invention pertains to methods and devices for strengthening the tongue and other muscles of the throat and upper airway. More specifically, the subject invention provides one or more embodiments of a threshold-load trainer, or similar device, for use in strengthening the muscles of the tongue to inhibit narrowing or obstruction of the upper respiratory airway. The threshold-load trainer embodiments of the subject invention can specifically target the genioglossus muscle (tongue protrude), so as to improve the strength and tonus in that muscle. This can inhibit the tongue from obstructing or narrowing the upper airway, particularly during a state of relaxation, such as during sleep. Strengthening the genioglossus muscle and other muscles of the mouth and throat can also aid in correcting or improving other medical conditions. The additional benefit of strengthening the genioglossus and geniohyoid muscle is improvement in the strength of the floor of the chin, which can reduce sagging tissue or double-chin appearance in that area. Additionally, the device can also be used with patients having neuromuscular disorders that affect swallowing or patient undergoing speech therapy to strengthen the muscles of the tongue.

The following description will disclose that the subject invention is particularly useful in the field of respiratory medicine, in particular the treatment and/or improvement of symptoms of Obstructive Sleep Apnea Syndrome (OSAS). However, a person with skill in the art will be able to recognize numerous other uses to which embodiments of the devices and methods of the subject invention could be applied. While the subject application describes, and many of the terms herein relate to, a use for treatment of OSAS, other modifications apparent to a person with skill in the art and having benefit of the subject disclosure are contemplated to be within the scope of the present invention.

In the description that follows, a number of terms are utilized. In order to provide a clear and consistent understanding of the specification and claims, including the scope to be given such terms, the following definitions are provided.

The term "patient" as used herein, describes a human.

Also, as used herein, and unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct, or indirect, physical or remote.

Finally, reference is made throughout the application to the "proximal end" and "distal end." As used herein, the proximal end is that end of the device that is nearest to the patient when the device is being used or that end that is placed in the mouth of the patient. Conversely, the distal end of the device is that end furthest from the patient when the device is being used in the mouth of a patient.

The present invention is more particularly described in the following examples that are intended to be illustrative only since numerous modifications and variations therein will be apparent to those skilled in the art. As used in the specification and in the claims, the singular for "a," "an" and "the" includes plural referents unless the context clearly dictates otherwise.

Figure 1B:
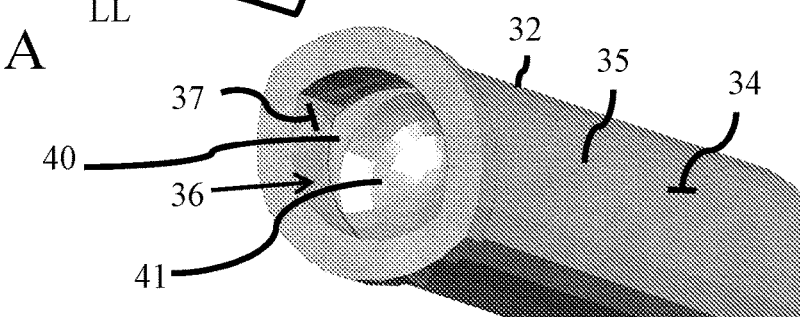

Reference will be made to the attached figures on which the same reference numerals are used throughout to indicate the same or similar components. With reference to the attached figures, which show certain embodiments of the subject invention, it can be seen in FIGS. 1A and 1B that, in general, threshold-load trainer 20 embodiments of the subject invention comprise a mouthpiece 30 that can be inserted into the mouth and a tongue resistance pad 40 within the mouthpiece against which the tongue can be pressed or exerted. A biasing element 60 can provide compression resistance to the tongue resistance pad. The compression resistance of the biasing element can be constant and/or adjustable. The tongue resistance pad can have an operable attachment to a force measuring device 200. The force measuring device can be further operably connected, permanently or temporarily, to a pressure transducer 300 that translates the force received by the tongue resistance pad into a discernable signal or indicator that correlates to the amount of pressure or compression being applied to the pressure pad by a tongue exerted against the tongue resistance pad. In a specific embodiment, the threshold-load trainer is modular, allowing components to be interchangeable or modified.

The mouthpiece 30 of a threshold-load trainer 20 can house or enclose a tongue resistance pad 40. When placed into the mouth of a patient, the mouthpiece can position a tongue resistance pad, so that the tip of the tongue can be exerted or pushed against the tongue resistance pad to target and strengthen the genioglossus muscle (GG), illustrated in FIG. 3. This can also strengthen other muscles of the mouth, throat and upper respiratory pathway. The configuration of the mouthpiece can be such that, when the proximal end 5 is inserted into the mouth of a patient, the mouthpiece can hold the jaws of a patient sufficiently apart to allow the tongue to pass between the upper and lower teeth. A mouthpiece can have one or more walls 35 that define a bore 36 in which the tongue resistance pad can reciprocate. In one embodiment the mouthpiece is rigid or semi-rigid, such that the lips, teeth, and/or tongue are inhibited from deforming the wall. The circumferential shape 32 of the outer surface 34 can vary, but is ideally configured to be comfortable to a patient. It can be adapted to comfortably fit the dental arch or part of the dental arch. For example, the circumferential shape can be round or oval to somewhat resemble the shape of the mouth when the jaws are separated. In a particular embodiment, the circumferential shape is oculiform, shown, by way of non-limiting example, in FIGS. 1, 5A, 5D, and 10A-10C.

Figure 2:
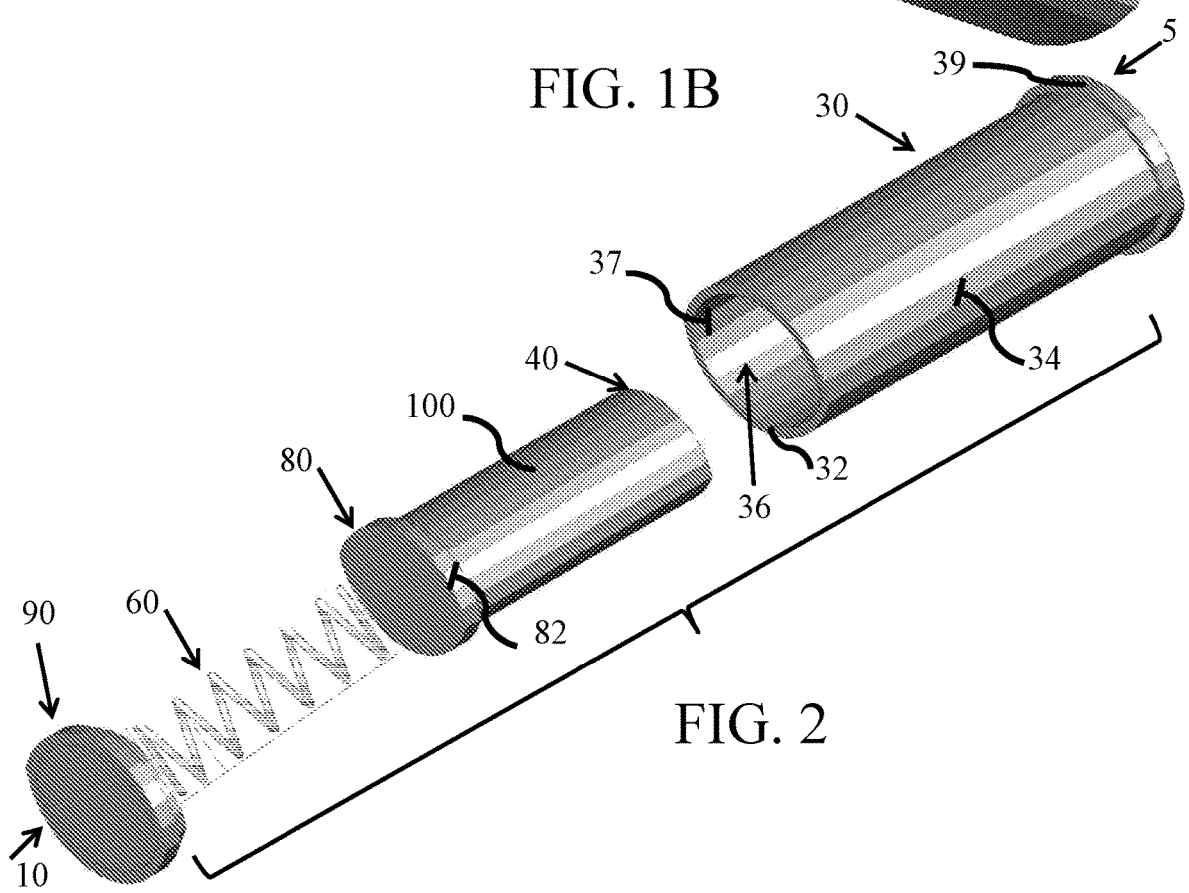
FIG. 2 illustrates an exploded view of one embodiment of a threshold-load trainer of the subject invention.
Figure 9:
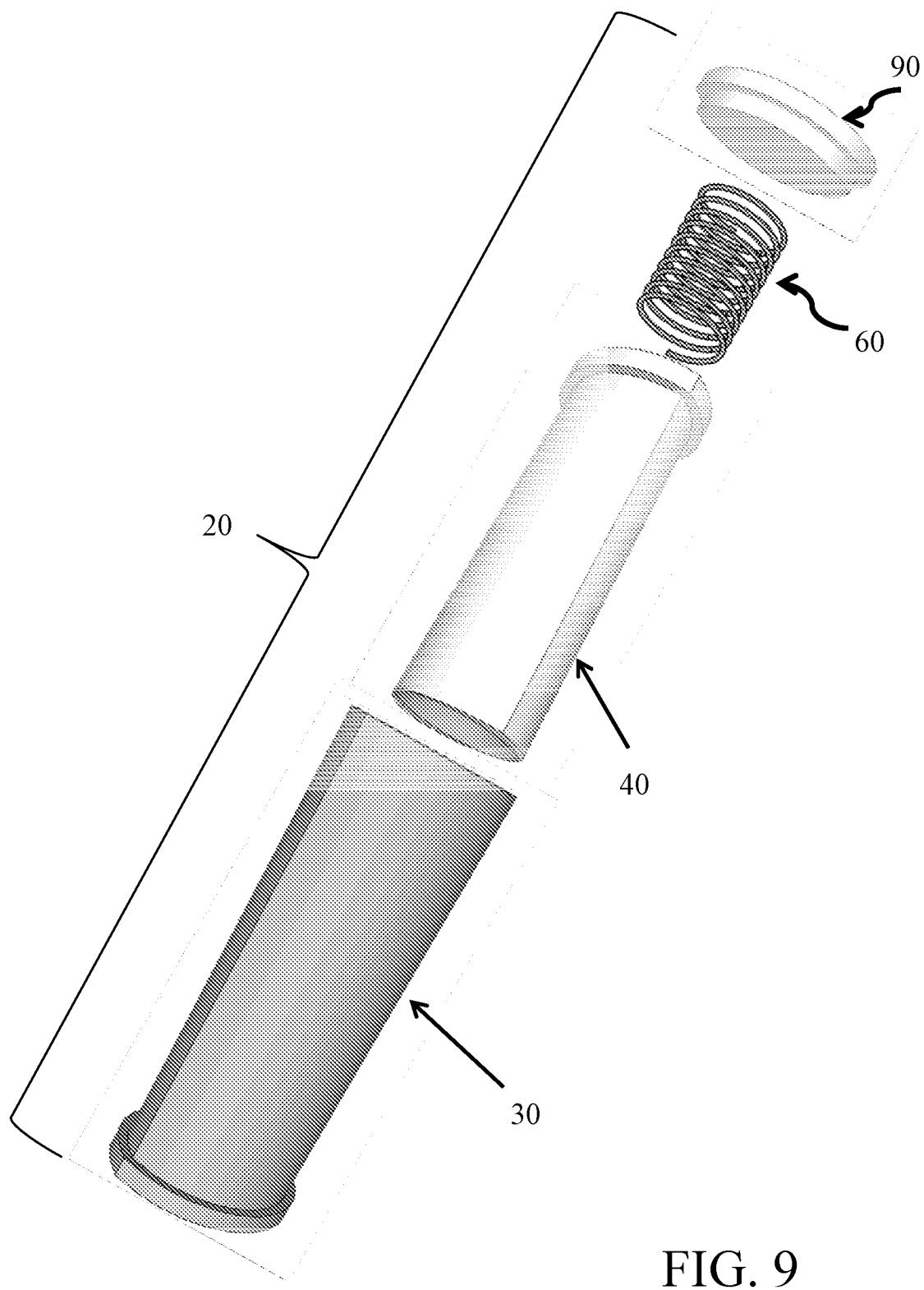
FIG. 9 is an exploded view of one embodiment of a threshold-load trainer of the subject invention. The mouthpiece and reciprocating plunger have been rotated relative to each other to illustrate the circumferential shapes.
Figures 10A, 10B, 10C:
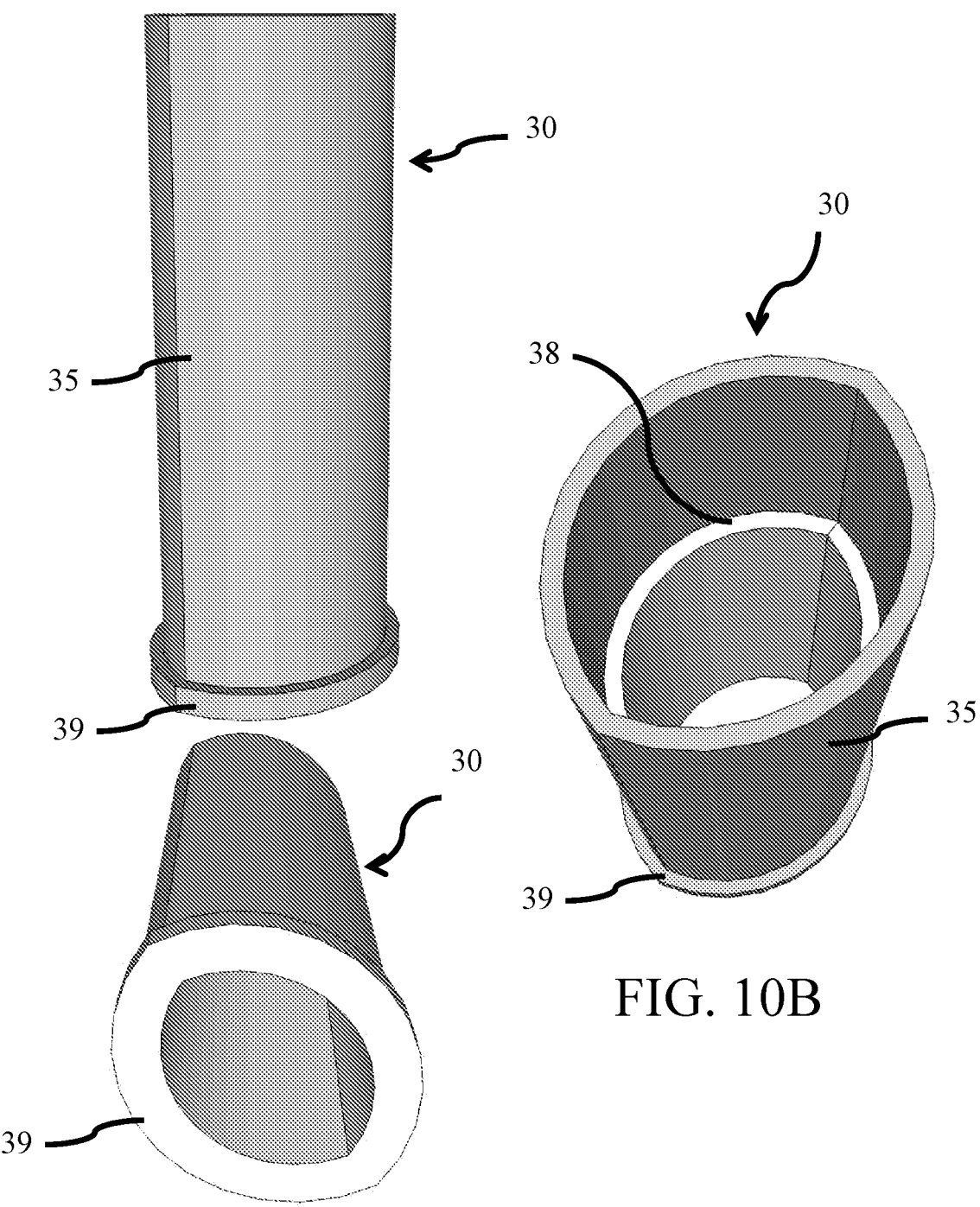
FIGS. 10A, 10B, and 10C illustrate a side elevation view, proximal end perspective view, and a distal end perspective view, respectively, of a mouthpiece embodiment of the subject invention.

The bore 36 can extend through the mouthpiece. At the proximal end, the bore is open to accommodate operation of a tongue resistance pad. The distal end can be open or closed, depending upon the configuration of one or more components within the bore. In one embodiment, the distal end 10 is sealed or closed, such that the bore is a blind-hole. In a more specific embodiment, the distal end 10 is closed with a cap 90 that can be made removable. This can be advantageous if it is necessary to have access to one or more components within the bore. It can also facilitate modularity, wherein components can be changed or modified. FIGS. 2 and 9 illustrate embodiments of a mouthpiece 30 with a cap 90. FIGS. 7A-7C and 12A-12B illustrate enlarged views of non-limiting examples of a cap that can be used with a mouthpiece.

Figure 5A:
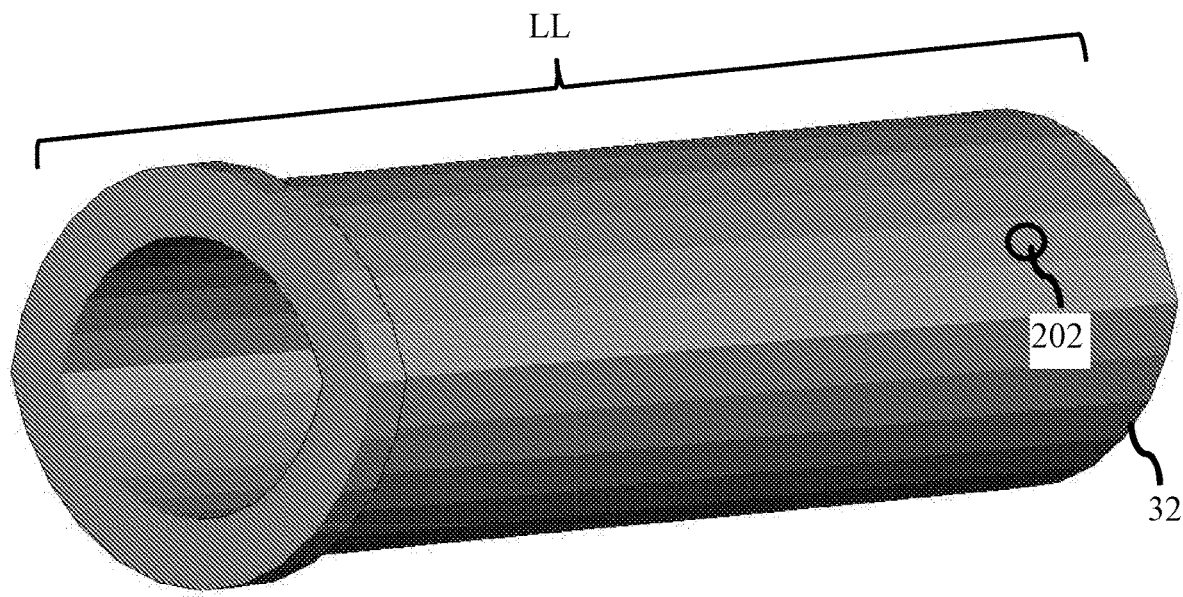
FIGS. 5A, 5B, 5C, and 5D illustrate an embodiment of a mouthpiece of a threshold-load trainer. This embodiment has a shelf-like stop within the bore and an opening for receiving a force measurement device.
Figure 5B:
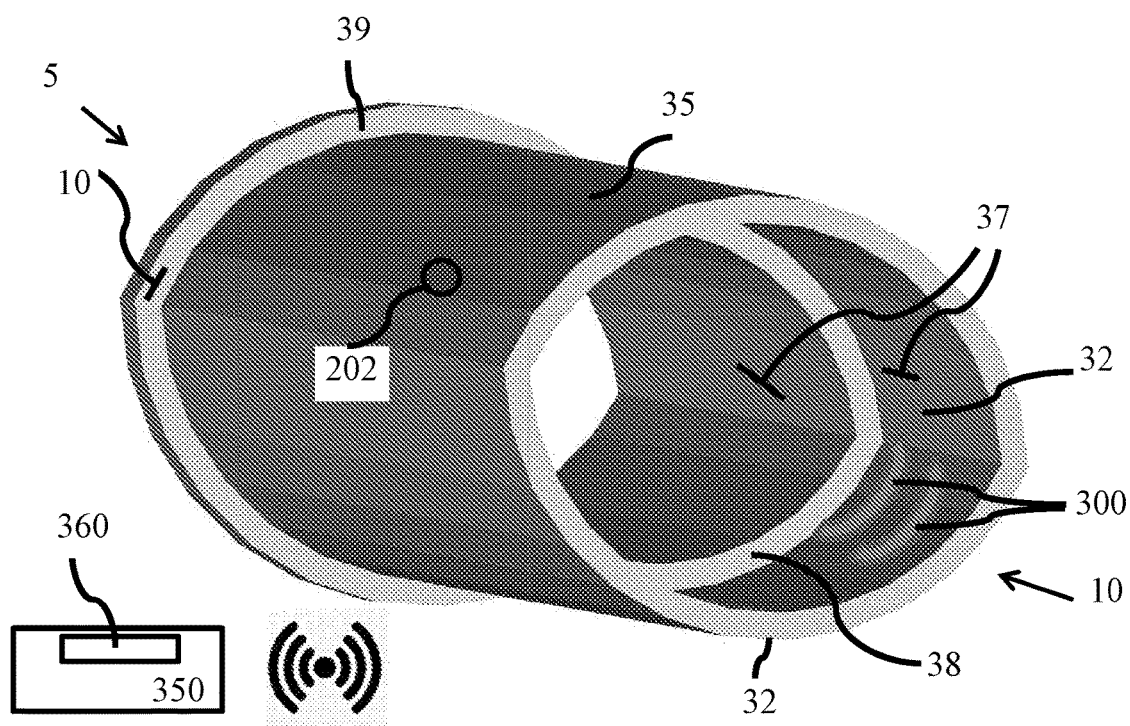
Figure 5C:
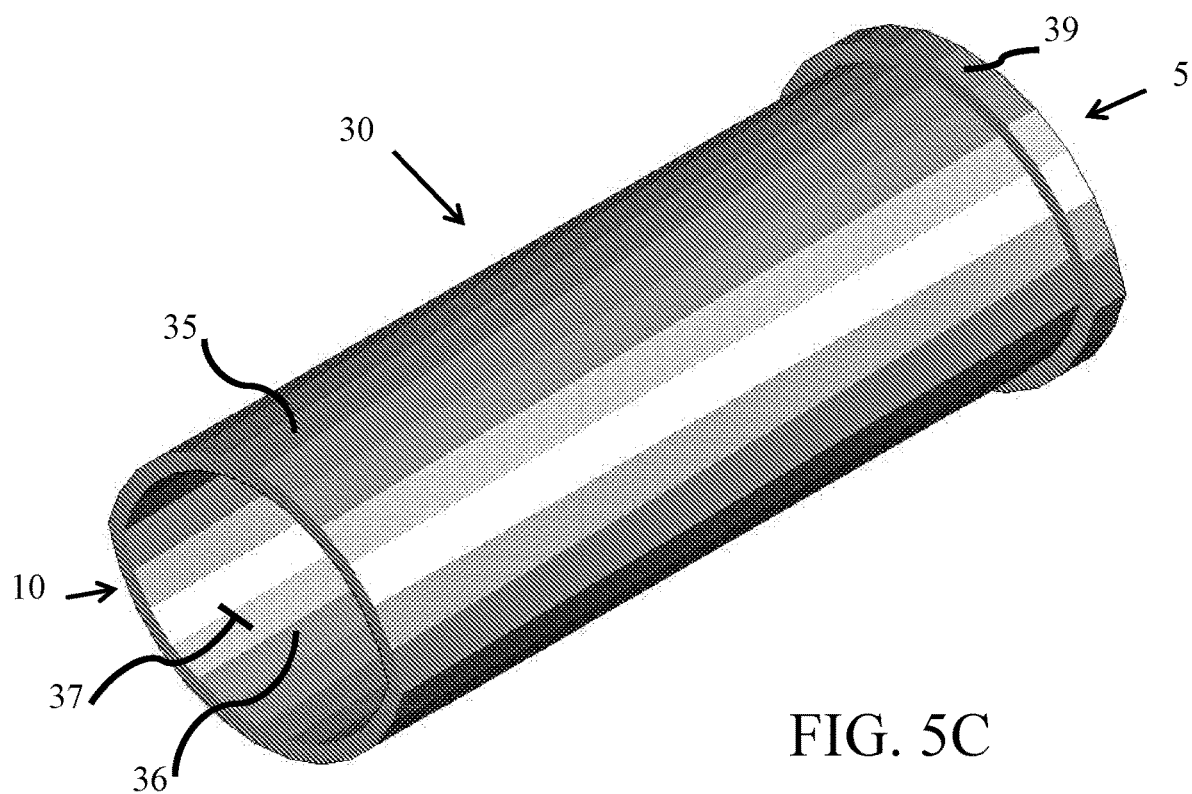
Figure 5D:
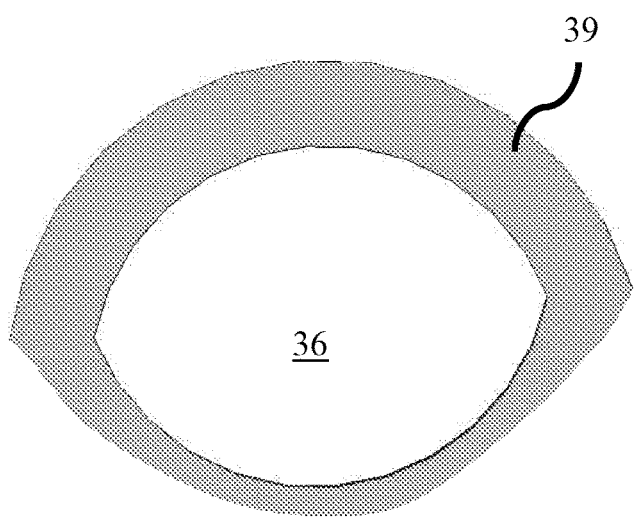

There can also be one or more retaining structures 39 that engage with the lips, teeth, or other areas of the mouth to inhibit the mouthpiece from being pushed out of the mouth, particularly when the tongue exerts pressure against the tongue resistance pad 40. By way of non-limiting example, there can be one or more retaining structures 37 located at or close to the proximal end 5 of the bore 32 that can be engaged by the lips, lingual or other surfaces of the teeth, or both to inhibit removal of the mouthpiece. Retaining structures 39 can be curved, arched, angled, or otherwise shaped and can rise above the outer surface 34, so that at least one of the lips and teeth can go over the retaining structures when the proximal end is inserted into the mouth. In one embodiment shown, by way of example, in FIGS. 1, 5A and 5C, the retaining structure 39 is a lip that rises above the outer surface 34. The lip can circumscribe the entire circumference of the outer surface, as shown in FIGS. 1, 5A, and 5C. Alternatively, the lip can circumscribe a portion of the outer surface. For example, that portion of the outer surface against which the front-most teeth make contact can have retaining structures, such as a partial lip. In another alternative, the retaining structures can rise to different heights above the outer surface. For example, a retaining structure that circumscribes the entire outer surface, such as the wall shown in FIGS. 1, 5A, and 5C, could be higher or rise further above the outer surface in one area and be less high or not rise as far above the outer surface in another area. By way of further example, a retaining structure 39 could be higher where the upper teeth would make contact with the mouthpiece. FIG. 5D illustrates a non-limiting example of this embodiment. The retaining structure can also have a shape that conforms to the teeth, lips, or shape of the mouth.

The bore 36 of a mouthpiece 30 can define the path and travel distance of a tongue resistance pad 40 located therein. The interior surface 37 of a bore can have the same circumferential shape 32 as the exterior surface 34. Alternatively, the interior surface of a bore can have a circumferential shape that is different from the circumferential shape of the exterior surface. By way of example, the exterior surface could be oculiform, as mentioned above, and the interior surface could be round or oval, or vice versa.

The bore 36 can contain or house one or more other components of the threshold-load trainer 20 in addition to the tongue resistance pad. For example, a stabilizer operable with the tongue resistance pad 40, a biasing element 60, one or more stops 38, and other components can be housed in the bore. It can be necessary to restrain or limit the motion of one or more of these other components in the bore. By way of non-limiting example, it can be beneficial if the tongue resistance pad has limited motion in the proximal direction, so that it does not protrude past the bore and into the mouth. By way of another non-limiting example, the biasing element could be restricted, so as to increase or decrease the amount of resistance that it applies to the tongue resistance pad. In a further example, the biasing element could be inhibited from falling out of the bore through the distal end 10.

In one embodiment, there is at least one stop 38 within the bore 30 that limits, restrains, restricts, or otherwise inhibits the motion of one or more other components within the bore. In a further embodiment, a stop extends from the interior surface 37, so that it protrudes or juts into the bore, acting as a barrier to the movement of one or more components. FIG. 5B illustrates one non-limiting example of a stop 38, wherein a portion of the interior surface 37 extends into the bore. In this example, the bore has different dimensions, so that it is narrower at one end, which creates a shelf stop between the two areas of different dimensions. One or more components in the bore can interact with this shelf stop to limit or inhibit movement past the shelf in one direction or the other.

Likewise, the dimensions of a mouthpiece can depend upon the configuration of other components of the threshold-load trainer. The longitudinal length LL, between the proximal end 5 and the distal end 10, should be adequate for insertion into the mouth, so that the teeth of a patient can be held apart by the mouthpiece. The longitudinal length can also be sufficient to inhibit the lips from coming together over or around the mouthpiece. Ideally, the longitudinal length is sufficient for insertion into the mouth without risk of swallowing or taking the entire threshold-load trainer 20 into the mouth. In one embodiment, the longitudinal length LL is between approximately 1.0 inch and approximately 5.0 inches. In more specific embodiment, the longitudinal length LL is between approximately 2.0 inches and 4.0 inches. The ability to determine an optimal longitudinal length is within the capability of one of ordinary skill in the art and will not be described in detail here. Variations in the longitudinal length that provide the same function, in substantially the same way, with substantially the same result are within the scope of the subject invention.

The teeth and lips can make contact with the proximal end 5 of the mouthpiece, as demonstrated by way of example in FIGS. 4A and 4B. Therefore, it can be beneficial if the areas on the mouthpiece contacted with the teeth and lips are comfortable and inhibit pain or injury to the tissues or teeth. The areas contacted with the teeth and lips can include one or more areas of the wall 35 and the retaining structure 39, which make up a bite area 33, as also shown, by way of example, in FIGS. 4A and 4B.

In one embodiment, the outer surface 34 of the wall 35 is made pliable or soft, so that it is susceptible to being indented, squeezed, mashed, or otherwise deformed for comfort. In a more specific embodiment, at least a portion of the outer surface of the bite area 33 is made pliable or soft, so that it can be indented, squeezed, mashed, or otherwise deformed for comfort. In one embodiment, a sleeve or band of pliable material can be installed over the more rigid material of the wall 35. In another embodiment, the wall or some portion thereof could also be coated with a suitable material. In yet another embodiment, the outer surface 34 of the wall or the bite area can be made of a pliable or soft material, by any of one or more techniques and methods known in the art. Materials having a lower durometer on most Shore scales could be used for covering a mouthpiece or portion thereof. There are numerous materials having suitable Shore durometers that could be utilized with the embodiments of the subject invention. A person with skill in the art will be able to determine the most appropriate material. Typically, when inserted into the mouth for use, the distal end 10 or surface of the retaining structure 39 will be placed near or against the labial surface of at least 2-8 of the front teeth. Conversely, the lips of the patient will be positioned at or near to the proximal end 5 or surface of the retaining structure, as shown, for example, in FIGS. 4A and 4B. Thus, the retaining structure can be similarly pliant and soft, as described above for the exterior surface of the bite area.

Figure 6A:
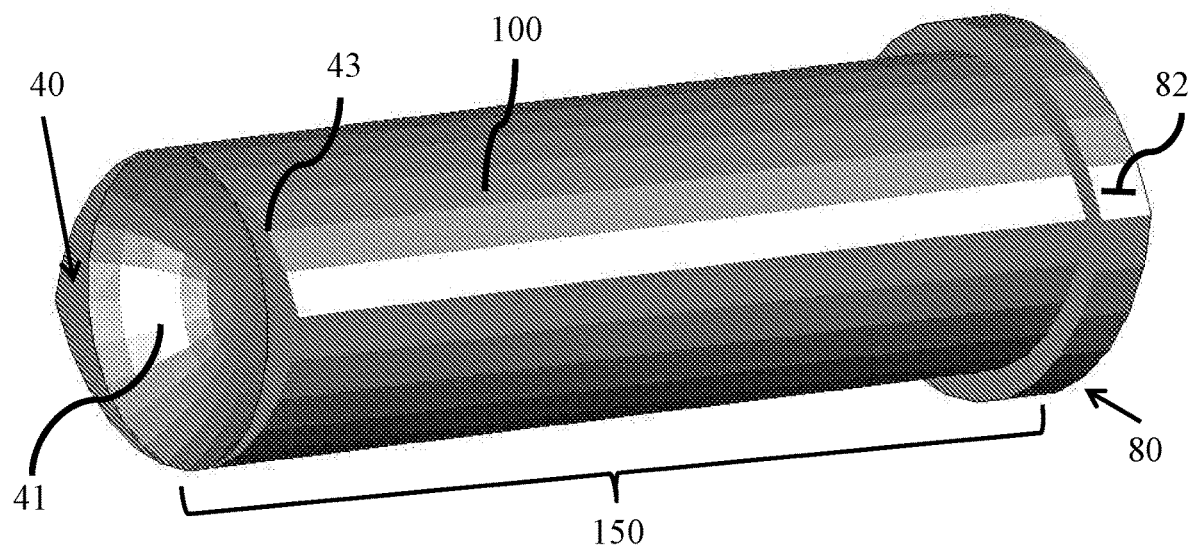
FIGS. 6A, 6B, 6C, 6D, and 6E illustrate embodiments of a reciprocating plunger that includes a tongue resistance pad, neck, and stabilizer.
Figure 6B:
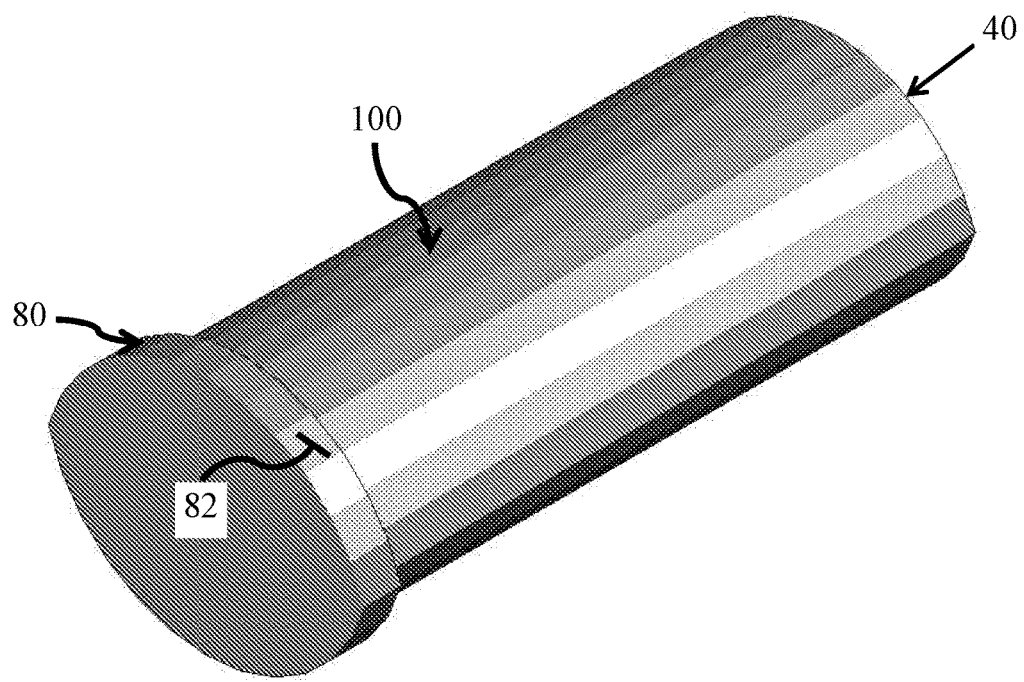
Figure 6C:
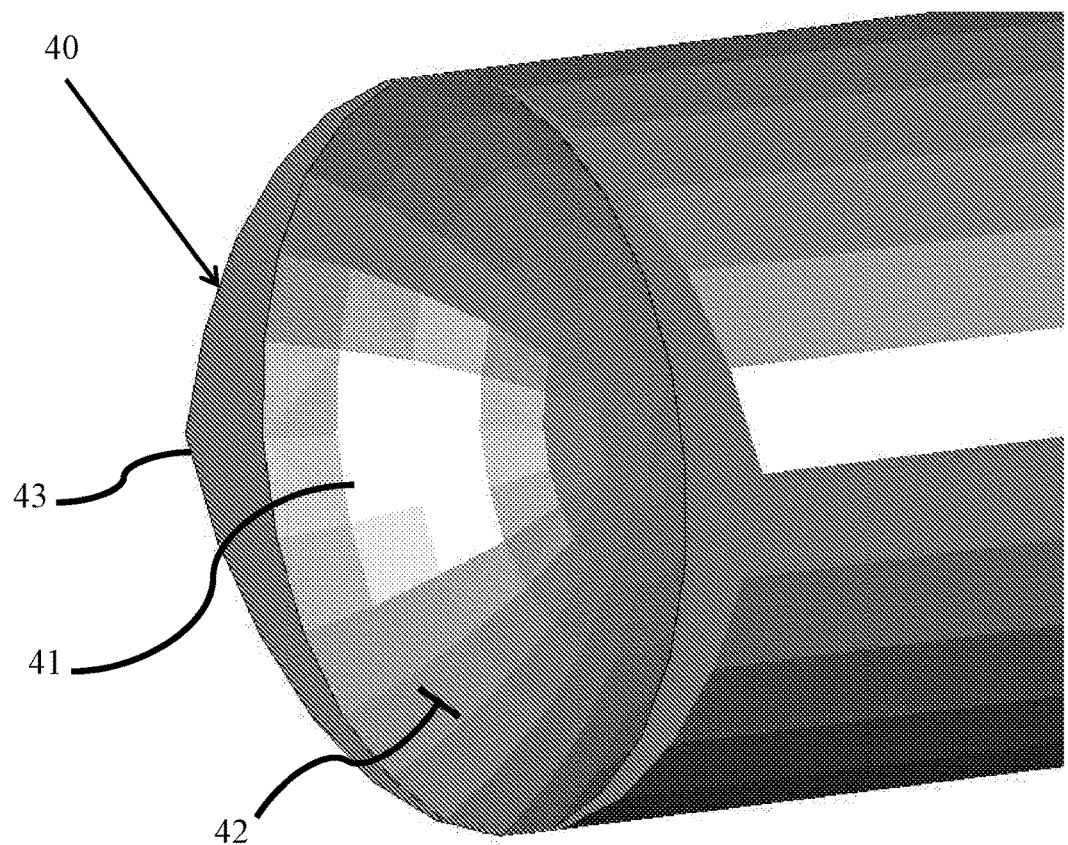

A tongue resistance pad 40 can be situated within the bore 36 at or near the proximal end of the mouthpiece. When the mouthpiece is placed in the mouth, the tongue can be exerted or pressed against the tongue resistance pad to effect a change in the position of the tongue resistance pad in the bore. Specifically, the tongue can be used to push the tongue resistance pad into the bore. The tongue resistance pad can have a contact surface 41 that faces or is directed towards the proximal end 5. The contact surface can have ergonomic or tactile features 42 that aid in placing the tongue in the correct position, inhibit the tongue from slipping off the contact surface, or provide other indications or assistance during training. FIGS. 6A and 6C illustrate an embodiment of a tongue resistance pad 40 having a tactile feature 42 that is a concave surface against which the tongue can be pressed during training.

Figure 6D:
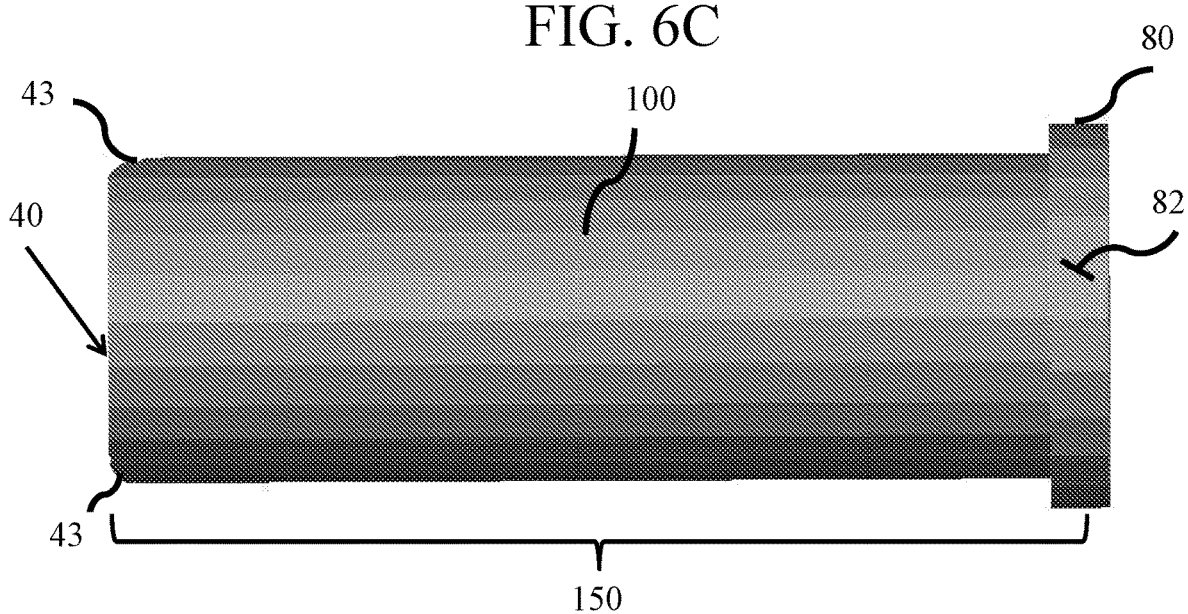
Figure 6E:
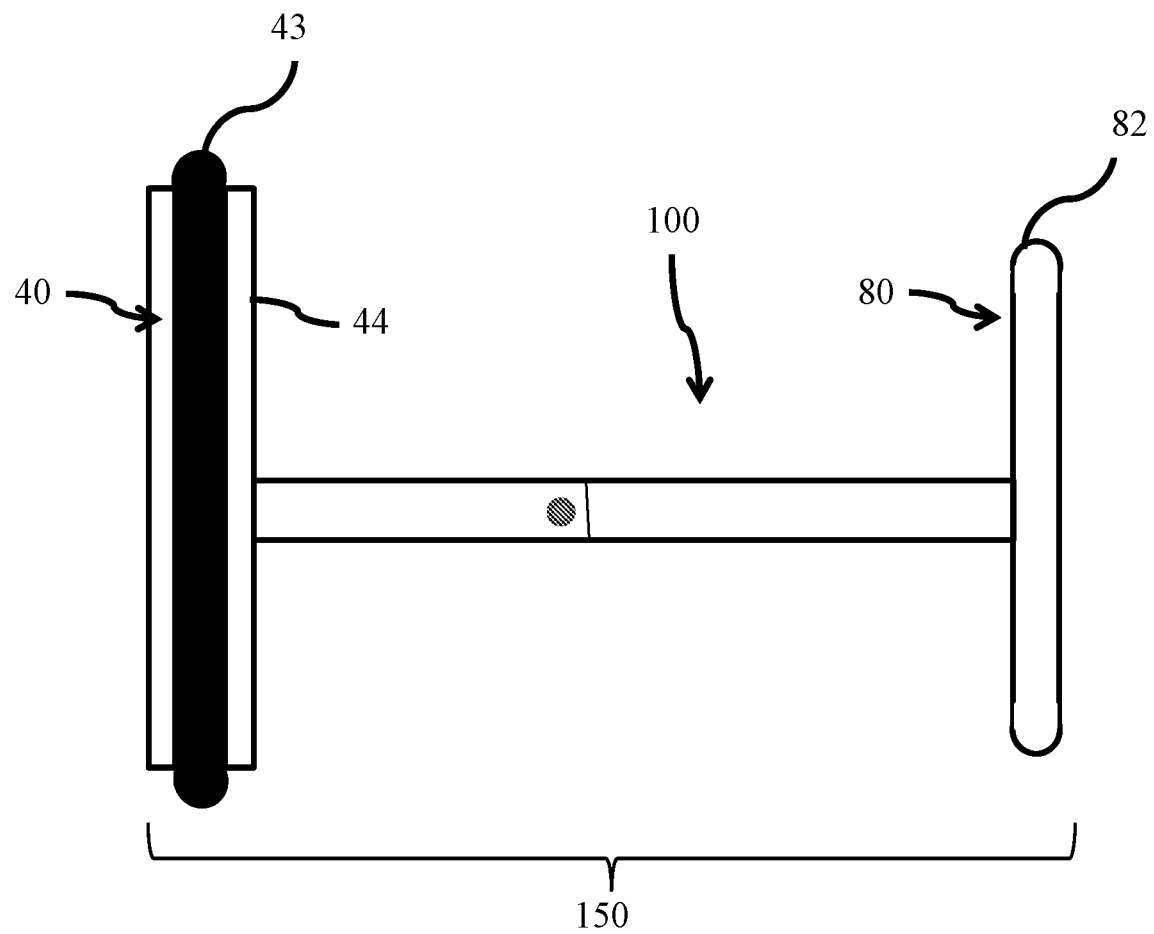
Figure 7A:
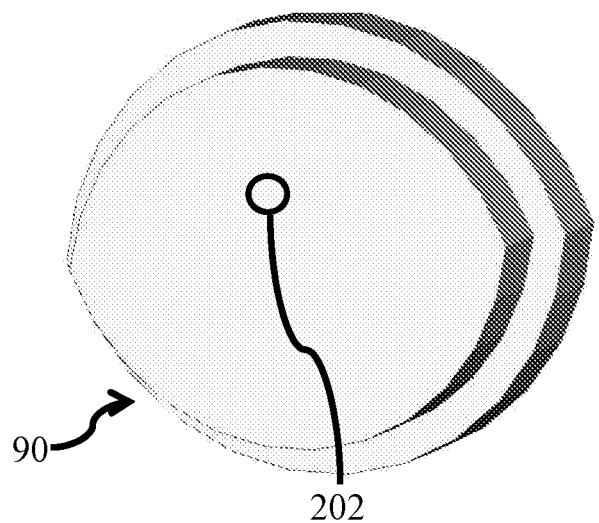
FIGS. 7A, 7B, and 7C illustrate one embodiment of a cap that can be used to close the distal end of a mouthpiece.
Figure 7B:
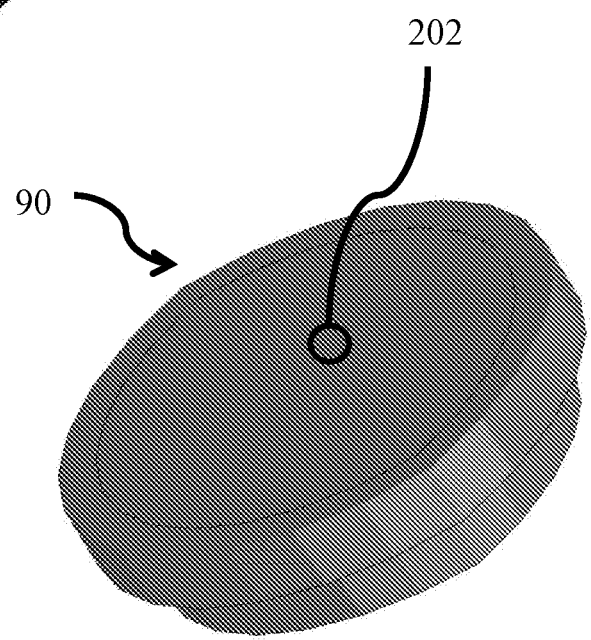
Figure 7C:
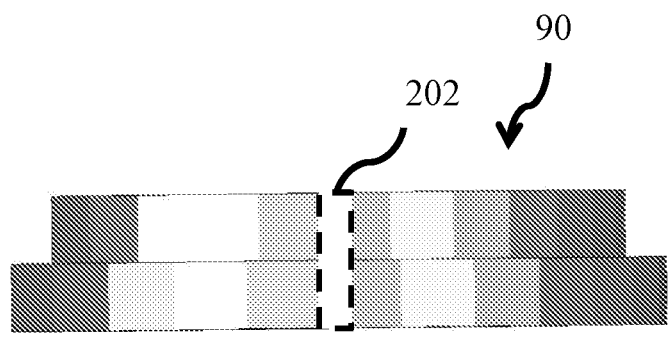

As the tongue protrudes into and out of the bore 36, against the tongue resistance pad 40, it is important to avoid pinching the tongue between the tongue resistance pad and the interior surface 37 of the bore 35. It can also be beneficial if the edge 43 of the tongue resistance pad does not jam or wedge in the bore. In one embodiment, the tongue resistance pad has one or more edges 43 that are curved or rounded to inhibit their being wedged against the bore wall if the tongue receiving pad becomes tilted or lopsided as it reciprocates within the bore. In one embodiment, the tongue resistance pad is formed with curved or rounded edges. In another embodiment, an O-ring, boot, band, or similar type of device is placed around one or more edges of the tongue receiving pad to provide curvature or roundness. FIGS. 6D and 6E illustrate an embodiment of a tongue receiving pad with curved or rounded edges.

Figure 8A:
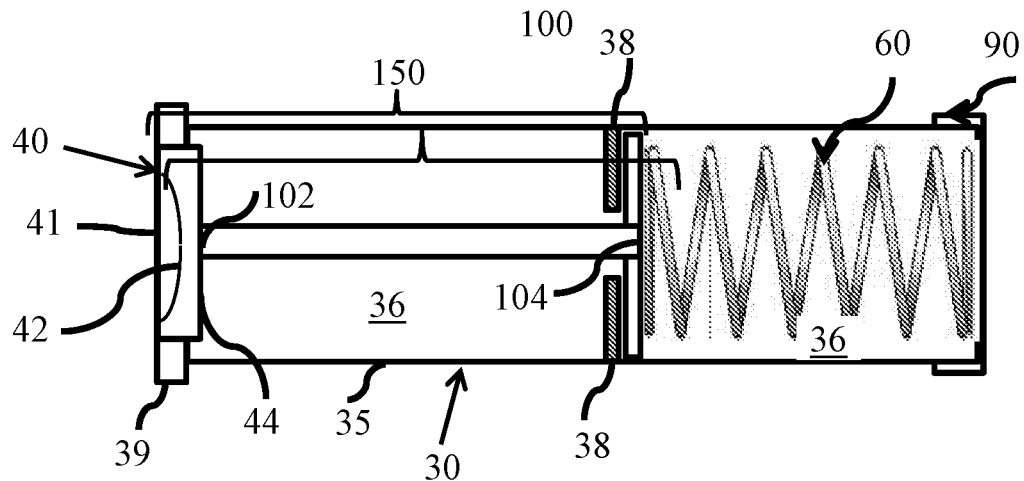
FIGS. 8A, 8B, and 8C are cross-section illustrations of embodiments of a threshold-load trainer of the subject invention.
Figure 8B:
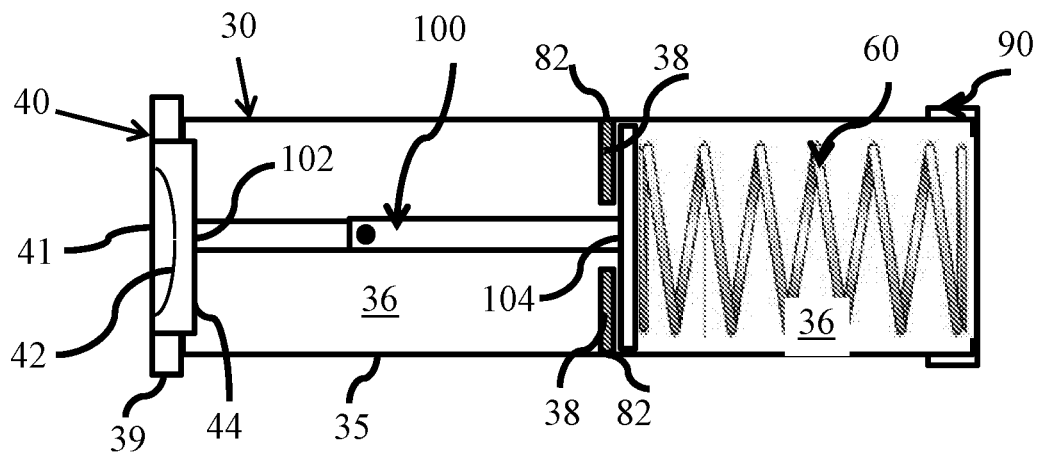
Figure 8C:
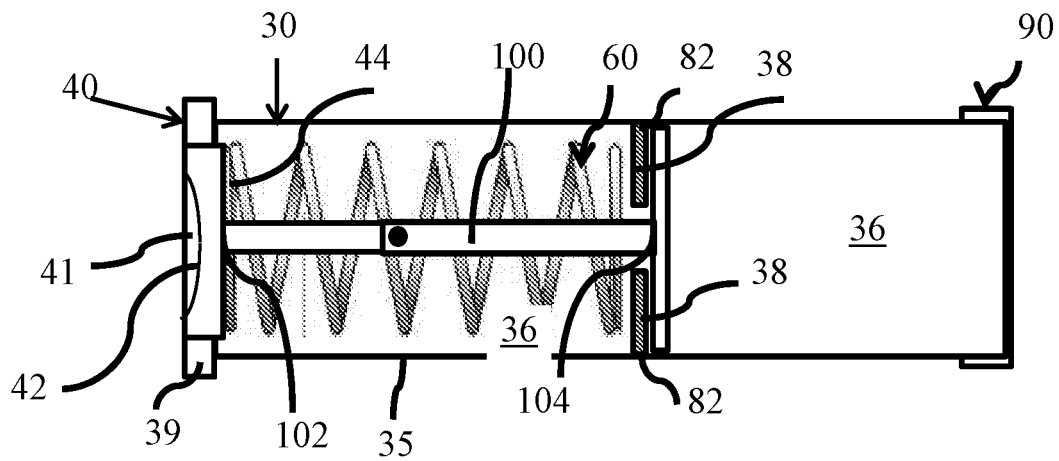

A threshold-load trainer device of the subject invention can be used to strengthen the muscles of the throat and upper respiratory pathway, muscles of the mouth and tongue muscles and can particularly target the genioglossus muscle (GG) under the tongue, which is illustrated in FIG. 3. As with any muscle, the genioglossus muscle can be strengthened by isometric and/or isotonic exercises. The tongue resistance pad 40 can be operably connected to a biasing element 60 that provides resistance or partial resistance to the tongue resistance pad. A biasing element can be any object, device, apparatus, material, or combination thereof capable of resisting or partially resisting an applied compression force. In one embodiment, a biasing element has shape memory characteristics, such that it can be temporarily changed in size, shape, or position and can return to the original size, shape, or position. In a particular embodiment, the biasing element provides increasing resistance, such that the more the biasing element is compressed, the greater the resistance. Examples of biasing elements are helical springs, Belleville washers, rubber or silicone pads and rings, pistons, balloons, leaf springs, elastic bands, and other devices known to those with skill in the art. The biasing element can be positioned in any suitable location within the mouthpiece and such location can depend upon the other components within the mouthpiece. In one embodiment, the biasing element is in direct contact with the tongue resistance pad, as shown in FIG. 8C. In another embodiment, the biasing element has an indirect contact with the tongue resistance pad, wherein other components are located between the tongue resistance pad and the biasing element, shown in FIG. 8B. The location of the biasing element within the bore is not a limiting factor, as long as the biasing element can function to provide compression resistance to the tongue resistance pad.

It can be advantageous if the resistance of the biasing element is adjustable. This can allow the resistance to be modified as necessary, and particularly as the tongue is strengthened. In one embodiment, the biasing element is a helical spring, shown for example in FIGS. 2, 4A and 4B. In one embodiment, the helical spring is removable from the bore, which allows it to be interchangeable with other helical springs of different compression force. For example, embodiments that utilize a cap 90 on the mouthpiece can provide access to the spring. In an alternative embodiment, one or more stops 38 can be used to adjust the compression resistance of a helical spring. As mentioned above, a stop 38 can arise from the interior surface 37 of the bore. Alternatively, a stop can be a device or mechanism that is placed in the bore that can operably attach to the biasing element to change the compression resistance. Other methods and devices for adjusting the load or compression resistance of a helical spring or other biasing elements are known in the art. Such variations that provide the same function, in substantially the same way, and provide substantially the same result, are within the scope of this invention.

As described previously, the edges 43 of a tongue resistance pad can be rounded or curved to inhibit wedging or jamming in the bore. To further ensure that the tongue resistance pad 40 remains aligned within the bore 36, so that it is inhibited from tilting and becoming wedged or jammed against the interior surface 37 when pressed inward by the tongue, a stabilizer 80 can be used with the tongue receiving pad. A stabilizer can be cooperatively engaged with the tongue resistance pad to confine the motion of the tongue resistance pad to be substantially perpendicular to the interior surface 37 of the bore 36. This can inhibit the tongue resistance pad from sliding unevenly or sideways through the bore, which can cause it to wedge or jam within the bore. Ideally, the tongue resistance pad and the stabilizer operate in tandem to keep each other aligned within the bore.

In a particular embodiment, the stabilizer can also interact with one or more stops 38 within the bore 36 to limit or constrain the range of motion of the tongue resistance pad. One embodiment of a threshold-load trainer 20 has a stop in the form of a shelf within the bore, as shown, for example, in FIG. 5B, and a stabilizer 80 having dimensions that cause it to abut against the shelf when the tongue receiving pad is not being pressed or pushed into the bore. FIG. 8A shows a non-limiting example of this embodiment. With this embodiment, the stabilizer can inhibit the tongue resistance pad from becoming jammed or wedged in the bore and also limits the range of motion of the tongue resistance pad, such that it is inhibited from extending past the proximal end 5 of the mouthpiece 30.

In one embodiment, a stabilizer has one or more interfacing surfaces 82 on or around the periphery that contact and slide against the interior surface 37 of the bore 36. In a further embodiment, the one or more interfacing surfaces and the interior surface have minimal tolerances therebetween, so as to inhibit tilting or slanting of the stabilizer and maintain alignment within the bore. FIGS. 6A and 6B illustrate one embodiment of a stabilizer 80 in the form of a rigid or semi-rigid plate with interfacing surfaces that are substantially parallel to the interior surface 37 of the bore. FIG. 6E illustrates an embodiment where the one or more interfacing surfaces 82 have curvature, which can further inhibit jamming or wedging of the stabilizer against the interior surface 37.

The stabilizer can be coupled to the tongue resistance pad 40. Such coupling can align the tongue receiving pad 40 with the stabilizer 80 allowing them to move in tandem to inhibit either or both from jamming or wedging within the bore. The tongue receiving pad and stabilizer can be coupled by any of a variety of structures or devices. Such coupling is, ideally, sufficiently rigid or confining to maintain alignment of the tongue receiving pad with the stabilizer as they reciprocate within the mouthpiece. In one embodiment, the tongue resistance pad is coupled to the stabilizer with a rigid or at least semi-rigid neck 100. The neck can have a first end 102 that is operably connected to the distal surface 44 of the tongue resistance pad and a second end 104 operably connected to the stabilizer 80. The combination of a tongue resistance pad 40, neck 100, and a stabilizer 80 can be referred to as a reciprocating plunger 150, since these components can move in tandem within the bore of the mouthpiece. FIGS. 11A-11C illustrate a non-limiting example of a reciprocating plunger. The neck can be a single, unitary object between the tongue resistance pad and the stabilizer, as shown, for example, in FIGS. 11A-11C. Alternatively, the neck can be of two or more sections, objects, or pieces between the tongue resistance pad and the stabilizer, as shown, for example, in FIG. 6E.

One embodiment, of a reciprocating plunger 150, shown in FIGS. 6A and 6D, has a columnar shaped neck with a diameter that is equivalent to or almost equivalent to the tongue resistance pad and/or the stabilizer. FIGS. 6A and 6D show a columnar neck integral with the edges of the tongue receiving pad. In another embodiment, the neck is more slender, such that the diameter is less than that of either or both the tongue resistance pad and the stabilizer. A specific embodiment has a neck that is rod- or post-like, which is illustrated in FIG. 8A. FIG. 8B illustrates an alternative embodiment of a post- or rod-like neck having more than one section, where the sections are connected between the tongue resistance pad and the stabilizer. In a particular embodiment, as shown, for example, in FIGS. 8A and 8B, the neck reciprocates between one or more stops 38, such as through a shelf stop 38, within the bore and connects to the stabilizer on the one side of the stop and the tongue resistance pad on the other side of the stop. FIG. 8C illustrates yet another embodiment where the neck 100 is a rod-like shape centered within a biasing element, which is a spring, and held in place by one or more stops 38. FIG. 8C shows the neck as more than one section, but it could be a single piece as well. The configuration of the neck is subject to variation and can depend upon numerous factors, known to those with skill in the art, for example, the location of stops within the bore, the position of the biasing element within the bore, the materials utilized, and other factors.

The dimensions of a reciprocating plunger 150 can depend upon, among other factors, the longitudinal length LL of the mouthpiece 30. In one embodiment, the reciprocating plunger is contained within the mouthpiece, such that it does not extend beyond the distal end 10 of the mouthpiece during use or otherwise. In an alternative embodiment, the reciprocating plunger extends, at least partially, past the distal end 10 of the mouthpiece. With either embodiment, it can be beneficial for the reciprocating plunger to move within the mouthpiece a sufficient distance to strengthen the genioglossus muscle and other muscles of the mouth, throat and upper respiratory pathway. In most instances, the tongue can be extended a few centimeters past the teeth to achieve adequate strengthening of the genioglossus muscle or other muscles of the mouth, throat and upper respiratory pathway. Thus, the dimensions of a reciprocating plunger should allow the tongue resistance pad 40 and the contact surface 41 to move between approximately 1.0 cm. to approximately 4.0 cm. into the bore 36, as measured from the proximal end 5. Thus, the dimensions of the mouthpiece 30 and reciprocating plunger 150 can be adjusted or adapted, as necessary, to provide sufficient movement of the tongue resistance pad within the bore.

In order to evaluate the strength of the genioglossus muscle, the amount of force applied to the tongue resistance pad can be measured. For example, force or compression measuring devices 200 are known in the art and can be operably connected to the tongue resistance pad by numerous methods. In one embodiment, there is a port 202 within the mouthpiece that leads into the bore, one example of which, is shown in FIGS. 5A and 5B. In another embodiment, there is a port 202 in the cap 90, which is shown, for example, in FIGS. 4A, 4B, and 7A-7C. The port can be used to make a direct or indirect contact or attachment between the tongue resistance pad 40 and the force measuring device. For example, some mechanical force measuring devices have a compression rod attachment that can be inserted into the port to measure the compression of at least one of the biasing element and stabilizer, which can be correlated to the amount of force being applied to the tongue resistance pad as it is being pushed by the tongue of a patient into the bore. FIG. 4A illustrates one example of this embodiment, where the compression rod 204 of a compression measuring device 200 is inserted into a port 202 in the cap 90 to make contact, direct or indirect, with the biasing element (i.e., the spring). As the tongue pushes against the tongue resistance pad, the biasing element 60 is compressed against the compression rod attachment, which relays data to the compression measuring device. The pressure measuring device can provide an observable indication of how much force is applied to the biasing element, which can be correlated to the amount of force applied by the patient's tongue to the tongue resistance pad.

Alternatively, there can be one or more sensors 300 located within the mouthpiece that are capable of transmitting data regarding the compression forces of the biasing element and/or the tongue resistance pad. For example, there can be multiple sensors within one or more walls 35 of the mouthpiece 30, as shown for example in FIG. 5B, that can be activated by one or more components in the bore, as the biasing element is compressed. By way of further example, the sensors can transmit information to a pressure transducer 350, which can translate the information and show results on a display 360 or provide some other discernable indicator or signal. There are numerous sensors, transducers, and other related devices available that can be used to transmit, receive, and display force-type data or information. The ability to determine an appropriate configuration for measuring compression force for an embodiment of a threshold-load trainer 20 is within the capability of one of ordinary skill in the art and will not be described in further detail here.

The genioglossus muscle is used to protrude or extend the tongue from the mouth. Strengthening this muscle can assist in alleviating symptoms of Obstructive Sleep Apnea Syndrome (OSAS). It can also improve the look of the neck and chin area. Additionally, the device can also be used to treat patients having neuromuscular disorders that affect swallowing, patients undergoing speech therapy or patients being treated for swallowing disorders to strengthen the muscles of the tongue (for example, the genioglossus and/or geniohyoid muscle).

The threshold-load trainer device embodiments of the subject invention can be used to target and strengthen the genioglossus muscle or muscles of the throat and upper respiratory pathway. By extending the tongue against a biased tongue resistance pad, the genioglossus muscle (or other muscles of the throat and upper respiratory pathway) can be trained and the tonus of the muscle can be increased so that it tends to hold the tongue away from the back of the throat during relaxation. By further measuring the amount of force applied by the tongue, the strength of the genioglossus muscle can be monitored and the threshold-load trainer can be adjusted.

It should be understood that the examples and embodiments described herein are for illustrative purposes only and that various modifications or changes in light thereof will be suggested to persons skilled in the art and are to be included within the spirit and purview of this application.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A device for strengthening the muscles of the tongue, comprising:
    a mouthpiece comprising a wall having a proximal end, a distal end, an exterior surface, and an interior surface that defines a bore;
    a tongue resistance pad within the bore, having a contact surface, an opposite distal surface, and at least one edge therebetween, the at least one edge being substantially perpendicular to the interior surface that defines the bore;
    a biasing element within the bore and in operable connection to the tongue resistance pad, where the biasing element biases the tongue resistance pad towards the proximal end of the bore;
    a stabilizer within the bore having at least one interfacing surface that is substantially perpendicular to the interior surface of the bore;
    a neck that operably connects the stabilizer to the tongue resistance pad to form a reciprocating plunger, such that the stabilizer, neck, and the tongue resistance pad operate tandemly within the bore when force is applied to the contact surface; and
    one or more retaining structures at the proximal end on the exterior surface of the mouthpiece;
    such that, when force is applied to the contact surface, the tongue resistance pad is depressed into the bore, whereby the biasing element provides compression resistance.

2. The device, according to claim 1, further comprising a removable cap at the distal end of the wall, such that the cap closes the distal end of the bore.

3. The device, according to claim 1, wherein the contact surface comprises tactile features.

4. The device, according to claim 1, wherein the biasing element is a helical spring.

5. The device, according to claim 4, further comprising one or more stops within the bore.

6. The device, according to claim 5, wherein the one or more stops arise from the interior surface of the bore.

7. The device, according to claim 5, wherein the one or more stops limit a motion of the reciprocating plunger by limiting a motion of the stabilizer within the bore.

8. The device, according to claim 7, further comprising:
    one or more sensors that measure a compression force applied to the biasing element and transmit data regarding the compression force; and
    a pressure transducer that receives the data from the one or more sensors and provides a signal pertaining to an amount of compression force being applied to the tongue resistance pad.

9. A method for strengthening one or more muscles of the tongue utilizing a device comprising a mouthpiece comprising a wall having a proximal end, a distal end, an exterior surface, and an interior surface that defines a bore; a tongue resistance pad within the bore, having a contact surface, an opposite distal surface, and at least one edge therebetween, the at least one edge being substantially perpendicular to the interior surface that defines the bore; a biasing element within the bore and in operable connection to the tongue resistance pad, where the biasing element biases the tongue resistance pad towards the proximal end of the bore; a stabilizer within the bore having at least one interfacing surface that is substantially perpendicular to the interior surface of the bore; a neck that operably connects the stabilizer to the tongue resistance pad to form a reciprocating plunger, such that the stabilizer, neck, and the tongue resistance pad operate tandemly within the bore when force is applied to the contact surface; and one or more retaining structures at or near the proximal end on the exterior surface of the mouthpiece; the method comprising:

a) inserting within the mouth of a patient in need of treatment the proximal end of the device, such that the one or more retaining structures are near or in contact with the labial surface of one or more teeth of the patient;

b) allowing the patient to exert force against the contact surface by pushing the tongue against the tongue resistance pad to depress the tongue resistance pad into the bore;

c) releasing the force of the tongue against the contact surface so that the biasing element returns the tongue resistance pad to a position at the proximal end of the bore; and d) repeating steps a) and c) for at least one of a predetermined amount of time and a predetermined number of repetitions.

10. The method, according to claim 9, further comprising measuring the amount of force applied to the tongue resistance pad by the tongue of the patient.

11. The method, according to claim 9, further comprising adjusting the biasing element to change the amount of compression resistance provided to the tongue resistance pad.

12. The method according to claim 9, wherein the patient: a) has a swallowing disorder; b) has a neuromuscular disorder that affects swallowing; or c) is undergoing speech therapy.

13. The method of claim 10, wherein the patient a) has a swallowing disorder; b) has a neuromuscular disorder that affects swallowing; or c) is undergoing speech therapy.

14. The method of claim 11, wherein the patient a) has a swallowing disorder; b) has a neuromuscular disorder that affects swallowing; or c) is undergoing speech therapy.

* * * * *